(12) United States Patent
Chou et al.

(10) Patent No.: US 9,972,189 B1
(45) Date of Patent: May 15, 2018

(54) PERSONAL RADIATION DOSIMETER AND ALERT SYSTEM

(71) Applicant: INTERNATIONAL BUSINESS MACHINES CORPORATION, Armonk, NY (US)

(72) Inventors: Philip Ju-Shuan Chou, Poughkeepsie, NY (US); Rajaram B. Krishnamurthy, Pleasant Valley, NY (US); Christine D. Mikijanic, Monroe, NY (US); Conner W. Simmons, Hopewell Junction, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days. days.

(21) Appl. No.: 15/351,649

(22) Filed: Nov. 15, 2016

(51) Int. Cl.
*G08B 21/12* (2006.01)
*G01J 1/42* (2006.01)
*G01J 1/02* (2006.01)

(52) U.S. Cl.
CPC ............ *G08B 21/12* (2013.01); *G01J 1/0219* (2013.01); *G01J 1/429* (2013.01)

(58) Field of Classification Search
CPC ........ G08B 21/12; G08B 21/14; G08B 21/24; G08B 21/182; G08B 25/00; G08B 25/016; A62B 9/006
USPC ...... 340/573.1, 539.11, 600; 250/336.1, 370, 250/370.01, 388, 392
See application file for complete search history.

(56) References Cited

U.S. PATENT DOCUMENTS

| | | | | |
|---|---|---|---|---|
| 4,320,393 A | | 3/1982 | Engdahl | |
| 4,489,315 A | * | 12/1984 | Falk | G01T 1/15 250/370.04 |
| 4,608,655 A | * | 8/1986 | Wolf | G01T 1/026 250/370.06 |
| 4,642,463 A | * | 2/1987 | Thoms | G01T 1/026 250/336.1 |
| 4,733,383 A | * | 3/1988 | Waterbury | G04G 21/02 368/10 |
| 6,765,214 B1 | * | 7/2004 | Kosslow | G01T 1/14 250/376 |
| 8,564,433 B2 | * | 10/2013 | Malkin | G01S 5/02 340/539.11 |

(Continued)

FOREIGN PATENT DOCUMENTS

CN 102334978 A 2/2012

OTHER PUBLICATIONS

Xia Wen, et al., "Investigation of Self-indicating Radiation Personal Dosimeter", Atomic Energy Science and Technology, vol. 48, No. 7, Jul. 2014; http://www.cnki.net; 4 pgs.

*Primary Examiner* — Hung T Nguyen
(74) *Attorney, Agent, or Firm* — Cantor Colburn LLP; Steven Chiu

(57) ABSTRACT

Methods, systems and computer program products for providing alerts to an individual based on their radiation level are provided. Aspects include receiving, by a processor, a radiation level of the individual from a dosimeter. Aspects also include obtaining, by the processor, schedule information for the individual. Aspects further include creating, by the processor, an alert based on the radiation level and the schedule information, wherein the alert includes a reminder of a precautionary measure that the individual should take based on the radiation level.

17 Claims, 4 Drawing Sheets

(56) References Cited

U.S. PATENT DOCUMENTS

| | | | |
|---|---|---|---|
| 9,024,271 B2 | 5/2015 | Aslam et al. | |
| 9,234,970 B2 | 1/2016 | Suzuki | |
| 2002/0079439 A1 | 6/2002 | Croydon et al. | |
| 2006/0097171 A1* | 5/2006 | Balchunas | G01T 1/169 250/336.1 |
| 2006/0170541 A1* | 8/2006 | Tompa | G01D 9/005 340/500 |
| 2007/0241261 A1* | 10/2007 | Wendt | G01D 9/005 250/221 |
| 2012/0268279 A1* | 10/2012 | Hatch | G01T 7/00 340/600 |
| 2013/0320220 A1 | 12/2013 | Donowsky | |

\* cited by examiner

PERSONAL RADIATION DOSIMETER AND ALERT SYSTEM

BACKGROUND

The present invention generally relates to a personal radiation detection device, and more particularly to methods and systems for using a personal radiation dosimeter to provide alerts to an individual regarding their radiation level.

Medical patients who require nuclear medicine have the side effect of becoming radioactive. These nuclear treatments may be radioactive iodine, permanent brachytherapy or even radiocontrast dyes for scans. The radiation can radiate from the source of the material, such as in permanent brachytherapy or it can be excreted in the body fluids in the case of radiocontrast dyes. In most cases, the radiation excreted does not pose imminent harm to the majority of the population. However, patients are advised to follow precautions to avoid radiation exposure to family and friends. Because every individual processes radiation differently, doctors tend to give generic precautions over a large time period to be safe. These precautions include washing clothes separately, using disposable utensils and avoiding prolonged contact with others. In general, patients undergoing nuclear medicine treatments may be preoccupied with their health situation and may forget to take the precautionary measures provided.

SUMMARY

In accordance with an embodiment, a method for providing alerts to an individual based on their radiation level is provided. The method includes receiving, by a processor, a radiation level of the individual from a dosimeter. The method also includes obtaining, by the processor, schedule information for the individual The method further includes creating, by the processor, an alert based on the radiation level and the schedule information, wherein the alert includes a reminder of a precautionary measure that the individual should take based on the radiation level.

In accordance with another embodiment, a computer program product for providing alerts to an individual based on their radiation level is provided. The computer program product includes a storage medium readable by a processing circuit and storing instructions for execution by the processing circuit for performing a method. The method includes receiving a radiation level of the individual from a dosimeter. The method also includes obtaining schedule information for the individual The method further includes creating an alert based on the radiation level and the schedule information, wherein the alert includes a reminder of a precautionary measure that the individual should take based on the radiation level.

In accordance with another embodiment, an electronic device for providing alerts to an individual based on their radiation level is provided. The electronic device includes a processor configured to receive a radiation level of the individual from a dosimeter and to obtain schedule information for the individual. The processor is also configured to create an alert based on the radiation level and the schedule information, wherein the alert includes a reminder of a precautionary measure that the individual should take based on the radiation level.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Embodiments include methods, systems, and computer program products for monitoring a radiation level of an individual and responsively providing alerts. In exemplary embodiments, a personal dosimeter monitors the level of radiation being emitted by an individual that has undergone nuclear medicine treatments. The personal dosimeter is in communication with a personal electronic device such as a smartphone, smartwatch, or the like. In exemplary embodiments, the personal dosimeter can be embedded in the personal electronic device. The personal electronic device receives the radiation level for the individual and provides alerts to the individual to remind the individual to take the necessary precautions based on the monitored radiation level. In exemplary embodiments, the personal electronic device uses information regarding the individual's schedule and activities, in addition to the radiation level, to determine what alerts to provide to the individual. The personal electronic device can obtain the individual's schedule and activities from one or applications on the personal electronic device, such as a calendar application or a social networking application, or from other sources. Further, the personal electronic device can notify the individual when the detected radiation level is low enough for the individual to resume normal daily activities.

Figure 1:
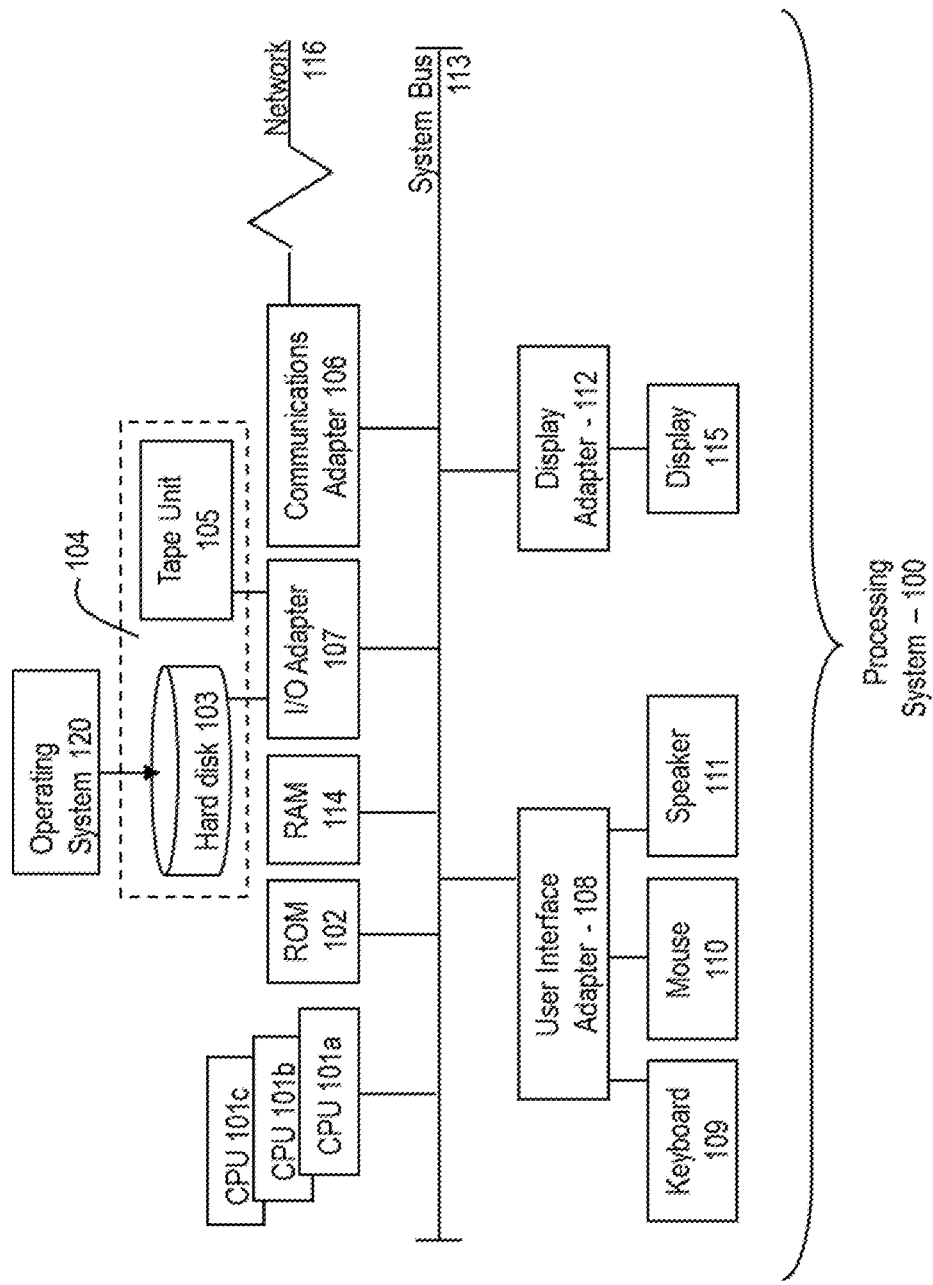
FIG. 1 is a block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 1, the processing system 100 includes processing capability in the form of processors 101, storage capability including the system memory 114 and mass storage 104, input means such as keyboard 109 and mouse 110, and output capability including speaker 111 and display 115. In one embodiment, a portion of system memory 114 and mass storage 104 collectively store an operating system to coordinate the functions of the various components shown in FIG. 1.

Figure 2:
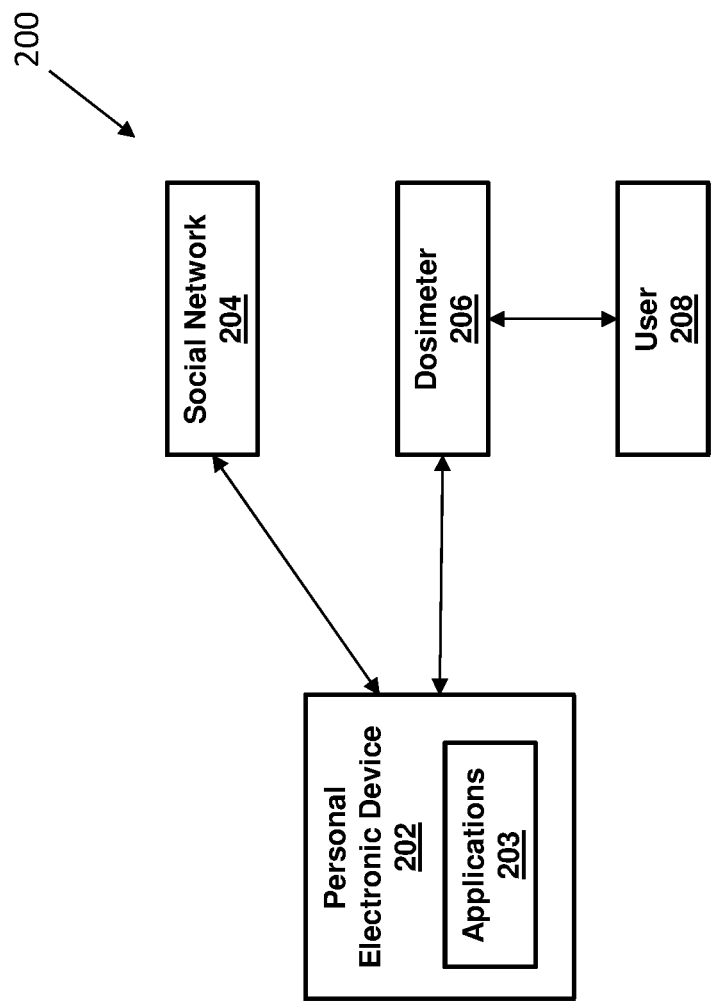
FIG. 2 is a schematic illustration of a personal radiation detection system in accordance with an embodiment.

Referring now to FIG. 2, a personal radiation detection system 200 in accordance with an embodiment is shown. As illustrated, the system 200 includes a personal electronic device 202, which can be a smartphone, a tablet, a processing system such as the one shown in FIG. 1, or any other suitable electronic device. The personal electronic device 202 is in communication with a dosimeter 206 that is configured to monitor a level of radiation being emitted by a user 208. In exemplary embodiments, the dosimeter 206 can communicate with the personal electronic device 202 via wireless communications methods, such as Bluetooth™ or WiFi™, or it can communicate with the personal electronic device 202 via wired communications.

In one embodiment, the dosimeter 206 is embodied in a wearable device that continuously monitors the radiation level of the user 208. In another embodiment, the dosimeter 206 is a standalone device that measures the radiation level of the user 208 periodically at the direction of the user and that communicates the measured radiation level to the personal electronic device 202. For example, the dosimeter 206 may be similar to a scale that an individual uses to periodically check their weight.

Figure 3:
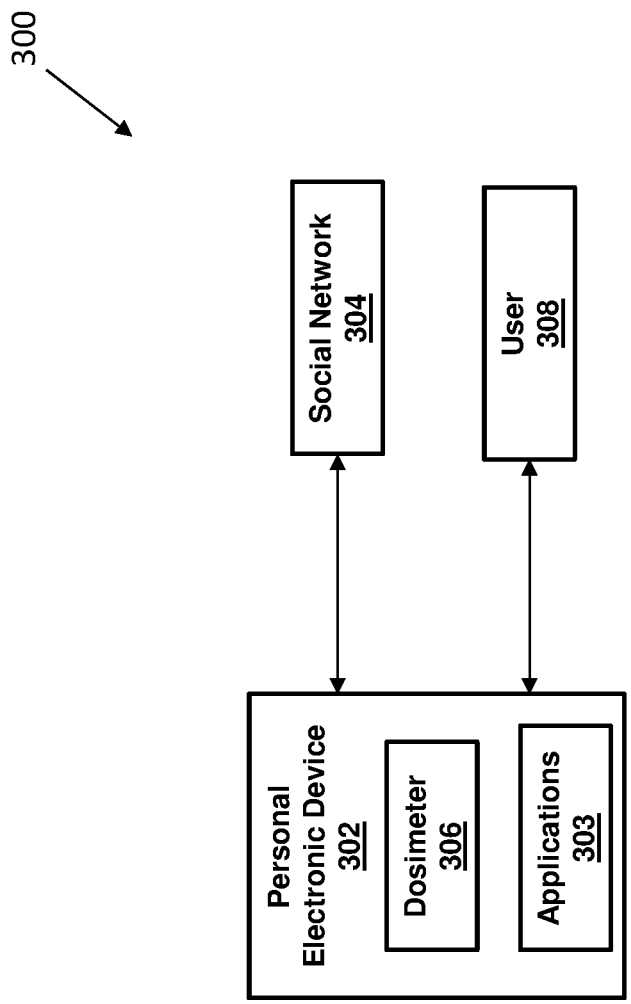
FIG. 3 is a schematic illustration of a personal radiation detection system in accordance with another embodiment.

Referring now to FIG. 3, a personal radiation detection system 300 in accordance with an embodiment is shown. As illustrated, the system 300 includes a personal electronic device 302, which can be a smartphone, a tablet, a processing system such as the one shown in FIG. 1, or any other suitable electronic device. The personal electronic device 302 includes a dosimeter 306 that is configured to monitor a level of radiation being emitted by a user 308.

In exemplary embodiments, the personal electronic device 202, 302 receives the radiation level of the user 208, 308 from the dosimeter 206, 306 and obtains additional information that is used to generate alerts to the user. The additional information obtained includes schedule information for the user 208, 308, such as places the user 208, 308 plans on going, activities that the user 208, 308 plans on doing, and individuals that the user 208, 308 will encounter and/or interact with. In exemplary embodiments, the schedule information can be obtained from applications 203, 303 on the personal electronic device 202, 302 such as calendar applications, email applications, contact databases and the like. In addition, the schedule information can be obtained from a social network 204, 304. The schedule information obtained from a social network 204, 304 can include a time and a location of an event that the individual will attend and an identity of one or more other individuals that will be at the event.

In exemplary embodiments, the personal electronic device 202, 302 generate alerts to the user 208, 308 to remind the user 208, 308 to take precautionary measures based on their radiation level. These precautions measures can include washing clothes separately, using disposable utensils and avoiding prolonged contact with others. For example, the alert may remind the person to only have contact with another individual for a specific period of time, where the length of the period of time is based on that individual's risk level for radiation exposure. In general, high-risk individuals, or those people that exposure to radiation may impact more severely than other, include infants, elderly and pregnant women. In one embodiment, the precautionary measures that are indicated by the alert can be determined based on the identity of the one or more other individuals that the user 208, 308 will encounter and based on the radiation level of the individual. In exemplary embodiments, the alerts may be displayed on a graphical display of the personal electronic device 202, 302 and may be accompanied by a sound or haptic alert to encourage the user 208, 308 to look at the graphical display of the personal electronic device 202, 302.

In exemplary embodiments, the personal electronic device 202, 302 may also access applications 203, 303 on the device such as calendars to check if the user 208, 308 will meet with high-risk individuals if the user 208, 308 plans on participating in activities that may cause the user 208, 308 to break their precautions. Such activities can include going to a laundromat or restaurant. The personal electronic device 202, 302 would then alert the user 208, 308 of the danger and remind them of their current precautions.

In exemplary embodiments, the personal electronic device 202, 302 may include an analytics engine that could analyze social networks 204, 304 to determine if an unplanned event may cause the user to break their precautions. For example, the user 208, 308 may be secluded in an area enjoying themselves and the analytics engine could analyze a social networks 204, 304 and notice that a large group of school children will be passing through the area. The personal electronic device 202, 302 would then alert the user 208, 308 of the danger and remind them of their precautions.

In some embodiments, the personal electronic device 202, 302 can be configured to send data relating to the radiation level of the user 208, 308 overtime to a central database. This central database can be used to obtain data regarding the rate at which the radiation level of different individuals. In exemplary embodiments, the radiation level data can be analyzed and used for purposes such as fine tuning the dose of nuclear medicine such that the ratio of medicine efficacy and post-treatment radiation could be optimized.

In exemplary embodiments, using a personal dosimeter, radioactive individuals are able to measure their own radioactivity. With these measurements, the individuals are reminded of precautions of interacting with certain high-risk individuals, such as children and pregnant women. In addition, in one embodiment, social networks 204, 304 that can use analytics to predict where the individual will go and remind the individual of their current precautions when interacting with people susceptible to radiation.

Figure 4:
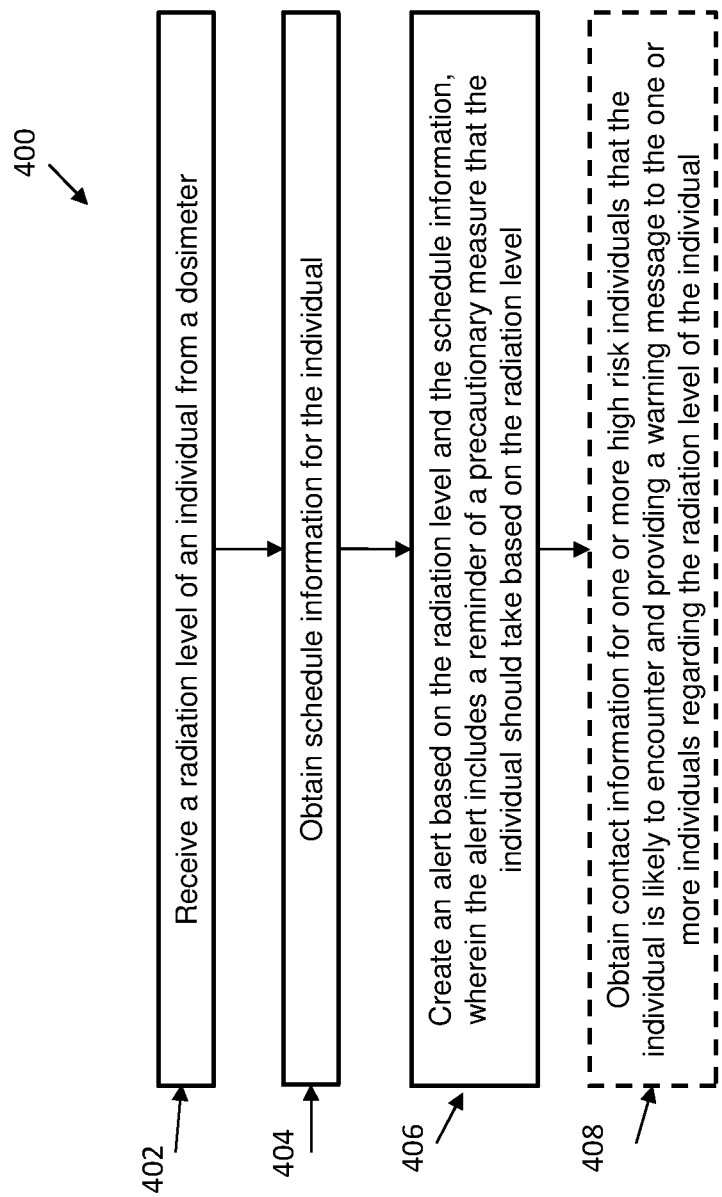
FIG. 4 shows a flow chart illustrating a method for using a personal radiation dosimeter to provide alerts to an individual regarding their radiation level in accordance with an embodiment.

Referring now to FIG. 4, a flowchart illustrating a method 400 for using a personal radiation dosimeter to provide alerts to an individual regarding their radiation level is shown. As shown at block 402, the method 400 includes receiving a radiation level of an individual from a dosimeter. In one embodiment, the dosimeter can be embodied in a wearable device, such as a smartwatch, that is in communication with a smartphone of the individual. In another embodiment, the dosimeter can be embodied in a smartphone of the individual. Next, as shown at block 404, the method 400 includes obtaining schedule information for the individual. In exemplary embodiments, the schedule information can be obtained from a calendar or from a social networking application that is accessible by the smartphone. The schedule information can include, but is not limited to, a time and a location of an event that the individual will attend and an identity of one or more other individuals that will be at the event.

Next, as shown at block 406, the method 400 includes creating an alert based on the radiation level and the schedule information. The alert includes a reminder of a precautionary measure that the individual should take based on the radiation level. In exemplary embodiments, the precautionary measure included in the alert is determined based on the identity of the one or more other individuals that will be at an event with the individual and based on the radiation level of the individual. Optionally, the method 400 can include obtaining contact information for one or more high-risk individuals that the individual is likely to encounter and providing a warning message to the one or more individuals regarding the radiation level of the individual, as shown at block 408. In exemplary embodiments, the one or more high-risk individuals that the individual is likely to encounter are identified based on data mining one or more social networks based on the schedule information for the individual.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for providing alerts to an individual based on their radiation level, the method comprising:
   receiving, by a processor, a radiation level of the individual from a dosimeter;
   obtaining, by the processor, schedule information for the individual;
   creating, by the processor, an alert based on the radiation level and the schedule information, wherein the alert includes a reminder of a precautionary measure that the individual should take based on the radiation level;
   obtaining contact information for one or more high-risk individuals that the individual is likely to encounter; and
   providing a warning message to the one or more high-risk individuals regarding the radiation level of the individual.

2. The method of claim 1, wherein the schedule information is obtained from a calendar application accessible by the processor.

3. The method of claim 1, wherein the schedule information is obtained from a social networking application accessible by the processor.

4. The method of claim 1, wherein the schedule information includes a time and a location of an event that the individual will attend and an identity of one or more other individuals that will be at the event.

5. The method of claim 4, wherein the precautionary measure is determined based on the identity of the one or more other individuals that will be at the event and based on the radiation level of the individual.

6. The method of claim 1, wherein the one or more high-risk individuals that the individual is likely to encounter are identified based on data mining one or more social networks based on the schedule information for the individual.

7. A computer program product embodied in a non-transitory computer readable medium for providing alerts to an individual based on their radiation level, the computer program product comprising:
   a storage medium readable by a processing circuit and storing instructions for execution by the processing circuit for performing a method comprising:
   receiving a radiation level of the individual from a dosimeter;
   obtaining schedule information for the individual;
   creating an alert based on the radiation level and the schedule information, wherein the alert includes a reminder of a precautionary measure that the individual should take based on the radiation levels;
   obtaining contact information for one or more high-risk individuals that the individual is likely to encounter; and
   providing a warning message to the one or more high-risk individuals regarding the radiation level of the individual.

8. The computer program product embodied in the non-transitory computer readable medium of claim 7, wherein the schedule information is obtained from a calendar application accessible by the processing circuit.

9. The computer program product embodied in the non-transitory computer readable medium of claim 7, wherein the schedule information is obtained from a social networking application accessible by the processing circuit.

10. The computer program product embodied in the non-transitory computer readable medium of claim 7, wherein the schedule information includes a time and a location of an event that the individual will attend and an identity of one or more other individuals that will be at the event.

11. The computer program product embodied in the non-transitory computer readable medium of claim 10, wherein the precautionary measure is determined based on the identity of the one or more other individuals that will be at the event and based on the radiation level of the individual.

12. The computer program product embodied in the non-transitory computer readable medium of claim 7, wherein the one or more high-risk individuals that the individual is likely to encounter are identified based on data mining one or more social networks based on the schedule information for the individual.

13. An electronic device for providing alerts to an individual based on their radiation level, including a processor configured to:
   receive a radiation level of the individual from a dosimeter;
   obtain schedule information for the individual;
   create an alert based on the radiation level and the schedule information, wherein the alert includes a reminder of a precautionary measure that the individual should take based on the radiation level;
   obtain contact information for one or more high-risk individuals that the individual is likely to encounter; and
   provide a warning message to the one or more high-risk individuals regarding the radiation level of the individual.

14. The electronic device of claim 13, wherein the schedule information is obtained from a calendar application accessible by the processor.

15. The electronic device of claim 13, wherein the schedule information is obtained from a social networking application accessible by the processor.

16. The electronic device of claim 13, wherein the schedule information includes a time and a location of an event that the individual will attend and an identity of one or more other individuals that will be at the event.

17. The electronic device of claim 16, wherein the precautionary measure is determined based on the identity of the one or more other individuals that will be at the event and based on the radiation level of the individual.

\* \* \* \* \*